United States Patent [19]

Verbeek et al.

[11] 4,385,124
[45] May 24, 1983

[54] REAGENT FOR THE QUANTITATIVE DETERMINATION OF WATER AND ITS USE THEREFOR

[75] Inventors: Antonie E. Verbeek, Bathmen; Jozef M. J. Mattheij, Deventer, both of Netherlands

[73] Assignee: J. T. Baker Chemicals B.V., Deventer, Netherlands

[21] Appl. No.: 339,120

[22] Filed: Jan. 13, 1982

[30] Foreign Application Priority Data

Jan. 22, 1981 [EP] European Pat. Off. ........ 81100469.6

[51] Int. Cl.³ ............................................. G01N 33/18
[52] U.S. Cl. ........................................ 436/42; 204/1 T
[58] Field of Search ...................... 23/230 R; 252/408; 204/1 T; 436/42

[56] References Cited

U.S. PATENT DOCUMENTS 2,967,155  1/1961  Blomgren et al. .................. 252/408
3,656,907  4/1972  Belmonte .......................... 252/408 X
4,295,990  10/1981 Verbeek et al. ............... 23/230 R X

OTHER PUBLICATIONS

Scholz, E., Karl Fischer-Reagentien ohne Pyridin, Fresenius Z. Anal. Chem. 303, 203-207, (Sep. 1980).
Verhoef et al., *J. Electroanal. Chem.*, 71 (1976) 305-315.
Peters et al., *Analytical Chemistry*, vol. 27, No. 3, 1955, pp. 450-453.

*Primary Examiner*—Arnold Turk
*Attorney, Agent, or Firm*—George W. Rauchfuss, Jr.

[57] ABSTRACT

Reagent for the quantitative determination of water, used together with an iodine-containing titrating solution, the reagent being free of pyridine and containing sulfur dioxide and an anhydrous alkali metal salicylate in methanol, 2-methoxyethanol or a mixture thereof in a volume ratio of at most 90 : 10 when a mixture of methanol and 2-methoxyethanol is used, which has been neutralized with an aliphatic amine for stabilizing the pH value.

This reagent is distinguished in that the increase of the blind value is restricted to a very low value even at elevated temperatures.

10 Claims, No Drawings

REAGENT FOR THE QUANTITATIVE DETERMINATION OF WATER AND ITS USE THEREFOR

BACKGROUND OF THE INVENTION

The usual method for quantitatively determining water is the Karl Fischer method in which the substance to be analyzed is reacted with sulfur dioxide and iodine dissolved in a mixture of pyridine and methanol; see K. Fischer, Angew. Chemie, vol. 48 (1935), page 394. The reagent reacts with water to give pyridine sulfate and hydrogen iodine. In this process the reagent undergoes decoloration. The iodine consumption is a measure for the water content of the substance. The reaction proceeds according to the following equation:

$$SO_2 + I_2 + 2H_2O \rightarrow H_2SO_4 + 2HI$$

The titrimetric determination is very accurate. The reagent allows a water content of less than 0.01% to be detected; see Kirk-Othmer, Encyclopedia of Chemical Technology, 2nd edition, vol. 2 (1963), pages 673–677.

A disadvantage of the Karl Fischer method is the fact that the reaction proceeds slowly, that titration is therefore laborious and time consuming and that the endpoint is distorted. An inconvenience is the annoying odor caused by the sulfur dioxide and pyridine. Moreover pyridine makes it necessary to perform the process under a fume hood. Another disadvantage is the yellow $SO_2I^-$ complex formed by the sulfur dioxide and iodide which excludes the visual determination of the end point.

The limited life, the unstable titer and the necessity of storage in the dark and under cool conditions are further drawbacks.

The limited possibilities of the use and the not very stable titration conditions are further problems which the analyst faces despite the fact that the Karl Fischer method has been substantially improved.

In a known further development of this Karl Fischer method the problems of the titrimetric determination of water are avoided; see J. C. Verhoef and E. Barendrecht, Analytica Chimica Acta, vol. 94 (1977), pages 395–403. This improved method makes use of two reagents, i.e. a solution of sodium acetate and sulfur dioxide in methanol (solution A) and a solution of iodine in methanol (titration solution B).

The so-called blind value of solution A is a measure of its stability. In practice it has been found that the blind value of solution A increases at 18° to 20° C. during a week by 0.1 ml. The reason is that the ester reaction proceeds according to the scheme:

alcohol + acid → ester + water

This reaction becomes more noticeable at higher temperatures.

In the present case the following esterification reaction takes place:

methanol + acetic acid → methyl acetate + water

Blind values of about 20 ml therefore appear especially in hot countries because of the ester reaction that takes place at the higher temperatures prevailing there, i.e. 0.4 to 0.5 ml of the solution A per month at 40° C. In the second or third month the increase is 0.5 to 1 to 2 ml of the solution A.

Because in titration acid is formed, the buffer capacity plays a very important part since the iodometric water determination is a redox titration which is heavily dependent on the pH-value.

The titration procedure is as follows: 20 ml of solution A are pretitrated with the titrating solution B under steady stirring and with moisture being excluded. A specified amount of the water-containing substance to be analyzed is then quickly placed into the titration vessel. The amount of the substance to be analyzed (amount of test sample) should be adequately proportioned to the estimated amount of water present.

With the appropriate buffer capacity, it is possible to determine 100 to 110 mg of water in 20 ml of solution A. The titration vessel is closed, the buret adjusted and titration is started. During the whole titration procedure the solution is to be thoroughly mixed with a magnetic stirrer.

The bipotentiometric method is used in the most usual titrations for determining the end point. The reduction time is normally 20 seconds, at which time the point of equivalence is reached.

With this method, aquametry without interference is possible in alcohols, alkanes, aromatic hydrocarbons, aldehydes, ketones, ethers, esters, salts with crystallization water, basic substances such as tris-(hydroxymethyl)-amino methane, lyophilized products, food, molecular sieves and granular fertilizers. This method also lends itself to the visual determination of the end point.

Thus the problem underlying the present invention is to develop a reagent for quantitatively determining water which is still stable even at elevated temperatures, e.g. 40° C., which reagent is based on the above-described known reagent solution A which is used together with the titrating solution B, and which when allowed to stand does not show an increase of the blind value even at elevated temperatures and results in minimum precipitations.

SUMMARY OF THE INVENTION

This problem is solved thanks to the surprising finding that when using methanol and/or 2-methoxyethanol as the solvent for the reagent solution A and simultaneous addition of an anhydrous alkali metal salicylate and sulfur dioxide, and when using an aliphatic amine for neutralizing the solution a stable reagent is obtained which, together with an iodine-containing titrating solution, can be used for the quantitative determination of water.

DETAILED DESCRIPTION OF THE INVENTION

Thus the invention relates to a reagent for the quantitative determination of water used together with an iodine-containing titrating solution, the reagent containing sulfur dioxide and an anhydrous alkali metal salicylate in methanol or 2-methoxyethanol or a mixture thereof as solvent, the volume ratio of a mixture of methanol and 2-methoxyethanol being at most 90:10, characterized in that the reagent has been neutralized with an aliphatic amine. This reagent (solution A) is used together with the above-described titrating solution B in a known manner for the quantitative determination of water.

Salicylic acid forms a good buffer in the form of a solution of, for example, sodium salicylate and salicylic acid. The solution A is formed by introducing sulfur dioxide into methanol or 2-methoxyethanol or a mixture thereof containing an alkali metal salt of the salicylic acid. A drawback of this solution is its pH value, which is too low as well as the annoying odor caused by free sulfur dioxide. As the solution A should not contain any free sulfur dioxide and the initial pH value should be adjusted to about 7, the solution is neutralized with an aliphatic amine, preferably diethanolamine or tris-(hydroxymethyl)-aminoethane.

For example, in the solution A the molarity for sodium salicylate is 1 mole and the molarity for sulfur dioxide is 0.5 mole. The solution is adjusted to a pH value of 7 by means of about 54.5 g diethanolamine or about 60 g tris-(hydroxymethyl)-aminoethane. The APHA color value of the solution A is 10 and the blind value is 0.5 to 3 ml titrating solution B for 20 ml of the solution A.

The titrating solution B has a constant titer of 3.5 mg $H_2O$/ml. Approximately 1 part titrating solution B is necessary for 2 parts of solution A.

The solution A of the invention contains an alkali metal salicylate preferably the sodium salt. The sodium salicylate serves above all as buffer and is employed in a molar amount of 1.5 to 0.5, preferably 1.2 to 0.8, and optimally 1.1 to 0.9. The sulfur dioxide is employed in a molar amount of 0.7 to 0.1, preferably 0.6 to 0.2, and optimally 0.55 to 0.45.

For stabilization the pH value is adjusted to 7.0±0.2 with the aliphatic amine. For this purpose, for example 76.3 to 10.9 g, preferably 65.4 to 21.8 g, and optimally 59.9 to 49.0 g of diethanolamine are necessary per liter or, for example 84 to 12 g, preferably 72 to 24 g, and optimally 66 to 54 g tris-(hydroxymethyl)-aminomethane.

The solvent used for the solution A and the titrating solution B, i.e. methanol, 2-methoxyethanol or a mixture thereof, should preferably be anhydrous. By anhydrous is understood here products with a water content of at most 0.05 percent by weight. Such products are commercially available.

If a mixture of methanol and 2-methyoxyethanol is used for the solution A, then the volume ratio is at most 90:10, preferably 85:15 to 75:25.

In practice the reagents for the determination of water are prepared in the following manner:

(a) First, nitrogen is introduced under stirring into anhydrous 2-methoxyethanol or into a mixture of anhydrous 2-methoxyethanol and anhydrous methanol for 15 to 30 minutes. In this way, small amounts of air or oxygen are separated from the solvent.

(b) The desired amount of anhydrous alkali metal salicylate (predried for 15 to 30 hours at 110° to 120° C.) is then added in small portions under stirring and is dissolved. At the same time nitrogen is blown into the solution.

(c) After the alkali metal salicylate has completely dissolved, nitrogen is introduced under stirring into the solution for another 15 to 30 minutes.

(d) Finally, the desired amount of sulfur dioxide is slowly introduced into the solution, yielding the solution A.

The titrating solution B is prepared in the following manner. Under stirring, the desired amount of iodine is introduced into anhydrous methanol or 2-methoxyethanol or a mixture thereof and dissolved in a closed system.

The two reagents of the invention keep well at room temperature or elevated temperatures as, for example 35° to 40° C., in tightly sealed bottles.

The following examples illustrate the invention.

EXAMPLE 1

Nitrogen is blown into 15.8 kg of anhydrous methanol for 15 minutes under stirring. 32 kg of dried sodium salicylate are then added under stirring and dissolved. After complete dissolution nitrogen is blown under stirring for another 15 minutes into the solution obtained. Then 6.4 kg of sulfur dioxide are slowly added within 3 to 4 hours. This solution is adjusted to a pH value of 7±0.2 by means of 12 kg of predried tris-(hydroxymethyl)-aminomethane. A solution A is obtained which can be used for the quantitative determination of water together with a titrating solution of iodine in methanol or 2-methoxyethanol or in a mixture thereof.

The titrating solution B is prepared in the following manner: 5.4 kg of iodine are dissolved in 79 kg of anhydrous methanol or 96 kg of anhydrous 2-methoxyethanol.

EXAMPLE 2

Solution A is prepared according to Example 1, however the pH value is adjusted to 7±0.2 by means of 10.9 kg of diethanol amine.

COMPARATIVE TEST 1

12.4 kg of dried sodium trimethylacetate and 16 kg of sodium salicylate are introduced in small portions under stirring into 15.8 kg of anhydrous methanol for 15 minutes. After complete dissolution nitrogen is blown under stirring for another 15 minutes into the solution obtained. 5.1 kg of sulfur dioxide are then slowly introduced within 3 to 4 hours. A solution A is obtained which can be used for the quantitative determination of water together with a titrating solution of iodine in methanol.

The titrating solution B has the same composition as in Example 1.

COMPARATIVE TEST 2

Nitrogen is blown under stirring into a mixture of 120.1 kg of anhydrous methanol and 36.5 kg of anhydrous 2-methoxyethanol. 15.6 kg of dried anhydrous sodium acetate are then added in small portions under stirring and dissolved. After complete dissolution nitrogen is blown into the solution obtained under stirring for another 15 minutes. 3.2 kg of sulfur dioxide are then slowly introduced within 3 to 4 hours. A solution A is obtained which can be used for the quantitative determination of water together with a titrating solution of iodine in methanol.

The titrating solution B has the same composition as in Example 1.

The table below shows the stability of the blind value (consumption of the titrating solution B per 20 ml of solution A) of the solutions A prepared according to Examples 1 and 2 and Comparative Tests 1 and 2.

TABLE

|  | EX. 1 | EX. 2 | Comp. Test 1 | Comp. Test 2 |
|---|---|---|---|---|
| Start (20° C.) | 1.21 ml | 1.34 ml | 1.50 ml | 1.20 ml |
| After 2 weeks | 1.21 ml | 1.34 ml | 1.50 ml | 1.40 ml |
| After 3 weeks | 1.22 ml | 1.34 ml | 1.55 ml | 1.60 ml |
| After 4 weeks | 1.23 ml | 1.35 ml | 1.60 ml | 1.80 ml |
| After 2 months | 1.23 ml | 1.60 ml | 1.80 ml | 2.80 ml |

TABLE-continued

|  | EX. 1 | EX. 2 | Comp. Test 1 | Comp. Test 2 |
|---|---|---|---|---|
| After 3 months At 40° C. | 1.23 ml | 1.60 ml | 2.70 ml | 3.80 ml |
| After 2 weeks | 1.21 ml | 1.45 ml | 1.50 ml | 2.20 ml |
| After 3 weeks | 1.22 ml | 1.50 ml | 1.60 ml | 3.70 ml |
| After 4 weeks | 1.23 ml | 1.50 ml | 1.70 ml | 4.00 ml |
| After 2 months | 1.29 ml | 1.65 ml | 2.10 ml | 10.50 ml |
| After 3 months At 5° C. | 1.32 ml | 1.90 ml | 2.60 ml | 15.00 ml |
| After 2 weeks | 1.21 ml | 1.34 ml | 1.50 ml | 1.20 ml |
| After 3 weeks | 1.21 ml | 1.34 ml | 1.50 ml | 1.20 ml |
| After 4 weeks | 1.21 ml | 1.34 ml | 1.50 ml | 1.20 ml |
| After 2 months | 1.21 ml | 1.34 ml | 1.50 ml | 1.20 ml |
| After 3 months | 1.21 ml | 1.34 ml | 1.50 ml | 1.20 ml |

As is evident from the table, the blind value remains stable for a prolonged period of time even at elevated temperatures (40° C.) thanks to the inventive composition of the reagent A, and consequently the problem posed of developing a stable solution for each working and storing temperature is successfully solved.

Test A

The reagent solution of Example 1 and the titrating solution B are used for determining water in petroleum ether having a boiling point of 100° to 140° C. The test is carried out in the following manner:

20 ml of the solution A are pretitrated with the titrating solution B while the contents of the reaction vessel are stirred and agitated and moisture is excluded. 25 ml of petroleum ether are then quickly placed into the titration vessel. After the titration vessel is closed and the buret is adjusted, titration is commenced. 0.18 ml of the titrating solution B are used up. This corresponds to a 0.004 percent water content of the petroleum ether.

Test B

Test A is repeated with the reagent solution of Example 2 and Comparative Tests 1 and 2. The following results are obtained:

Water content of the petroleum ether
using the reagent solution of Example 2=0.004 percent
using the reference solution 1=0.004 percent
using the reference solution 2=0.004 percent In further tests—carried out according to Test A—the reagent solution A of Examples 1 and 2 and the reference solutions 1 and 2 are used for determining the water content of edible oil. 10 ml of edible oil are used and 1.13 ml of the titrating solution B are used up.

In Example 1 this corresponds to a water content of 0.05 percent.

In Example 2 this corresponds to a water content of 0.05 percent.

In reference solution 1 this corresponds to a water content of 0.05 percent.

In reference solution 2 this corresponds to a water content of 0.05 percent.

The different capacity for the determination of water per 20 ml of the different reagent solutions A of Examples 1 and 2 and reference solutions 1 and 2 is as follows:

20 ml of the solution A are pretitrated with the titrating solution B while the contents of the reaction vessel are stirred and agitated and moisture is excluded. 5 ml of methanol/water standard solution (1 ml=1 mg water) are in each case quickly placed into the titration vessel until the capacity end point is reached. At this point the reaction is very slow.

The results of the water determination capacity in 20 ml of the reagent solution A are as follows:

For Example 1:100 to 110 mg of water
For Example 2:100 to 110 mg of water
For reference solution 1:70 to 80 mg of water
For reference solution 2:40 to 50 mg of water

We claim:

1. A reagent for the quantitative determination of water, used together with an iodine-containing titrating solution, said reagent comprises sulfur dioxide, an anhydrous alkali metal salicylate and a solvent selected from the group consisting of methanol, 2-methoxyethanol and mixtures thereof, the volume ratio being at most 90:10 when a mixture of methanol and 2-methoxyethanol is used, said reagent has been neutralized to a pH of 7.0±0.2 with an aliphatic amine and said reagent being free of pyridine.

2. A reagent according to claim 1, characterized in that the amine is tris-(hydroxymethyl)-aminomethane.

3. A reagent according to claim 1, characterized in that the amine is diethanolamine.

4. A reagent according to claim 1, characterized in that the anhydrous alkali metal salicylate is sodium salicylate.

5. A reagent according to claim 2, characterized in that the anhydrous alkali metal salicylate is sodium salicylate.

6. A reagent according to claim 3, characterized in that the anhydrous alkali metal salicylate is sodium salicylate.

7. A reagent according to claim 1 wherein the amine is employed in the reagent in an amount of from about 76.3 to about 10.9 g per liter.

8. A reagent according to claim 2 wherein the amine is employed in the reagent in an amount of from about 76.3 to about 10.9 g per liter.

9. A reagent according to claim 3 wherein the amine is employed in the reagent in an amount of from about 76.3 to about 10.9 g per liter.

10. A reagent according to claim 4 wherein the amine is employed in the reagent in an amount of from about 76.3 to about 10.9 g per liter.

* * * * *